United States Patent
Hahn et al.

(10) Patent No.: US 6,243,436 B1
(45) Date of Patent: Jun. 5, 2001

(54) CT DEVICE FOR IMAGING SLICES THAT ARE INCLINED TOWARD THE SYSTEM AXIS

(75) Inventors: Guenter Hahn, Shanghai (CN); Rolf Hupke, Eckental (DE)

(73) Assignee: Siemens Aktiengeseuschaft, Munich (DE)

( * ) Notice: Subject to any disclaimer, the term of this patent is extended or adjusted under 35 U.S.C. 154(b) by 0 days.

(21) Appl. No.: 09/516,885

(22) Filed: Mar. 2, 2000

(30) Foreign Application Priority Data

Mar. 4, 1999 (DE) ................................ 199 09 527

(51) Int. Cl.⁷ ........................................ H05G 1/64
(52) U.S. Cl. .................................... 378/4; 378/15
(58) Field of Search .................... 378/4, 14, 17, 378/195, 196, 21, 26, 27, 25; 382/131; 328/128, 132, 278, 280

(56) References Cited

U.S. PATENT DOCUMENTS

| | | |
|---|---|---|
| 4,246,484 | 1/1981 | Fetter . |
| 5,247,556 * | 9/1993 | Eckert et al. .............................. 378/4 |
| 5,430,783 * | 7/1995 | Hu et al. ................................. 378/15 |
| 5,463,666 * | 10/1995 | Eberhard et al. ......................... 378/4 |
| 5,722,408 | 3/1998 | Dehner et al. . |
| 5,943,434 * | 8/1999 | Schwarz ................................ 382/131 |

\* cited by examiner

*Primary Examiner*—Robert H. Kim
*Assistant Examiner*—Irakli Kiknadze

(57) ABSTRACT

A CT device for imaging slices that are inclined toward the system axis has an input unit for the entering the position of at least one slice that is to be imaged and that is inclined toward the system axis. A volume which completely contains the slice that is to be imaged and that is inclined toward the system axis is scanned by initially generating planar tomograms from the data acquired during the scanning of the volume, and the tomogram of a desired slice that is inclined toward the system axis is produced from these planar tomograms by multi-planar reconstruction.

7 Claims, 3 Drawing Sheets

CT DEVICE FOR IMAGING SLICES THAT ARE INCLINED TOWARD THE SYSTEM AXIS

BACKGROUND OF THE INVENTION

1. Field of the Invention

The present invention is directed to a CT (computed tomography) device of the type for imaging slices that are inclined toward the system axis with a measuring unit having a detector system and an X-ray source that is displaceable around a system axis for scanning an examination subject, whereby the examination subject and the measuring unit can be adjusted relative to one another in the direction of the system axis for scanning a volume of the examination subject.

2. Description of the Prior Art

CT devices of this general type are known wherein the measuring unit is tilted relative to the system axis for imaging slices that are inclined toward the system axis.

A disadvantage of such known devices is the considerable technical outlay that is associated with the realization of a measuring unit that can be tilted.

SUMMARY OF THE INVENTION

An object of the present invention is to provide a CT device of the type described above wherein the imaging of slices inclined toward the system axis is possible with reduced technical outlay.

According to the invention, this object is achieved in a CT device for imaging slices inclined toward the system axis with a measuring unit having a detector system and a radiation source that is displaceable around a system axis for scanning an examination subject, whereby the examination subject and the measuring unit are adjustable relative to one another in the direction of the system axis for scanning a volume of the examination subject, and having an input means for entering the position of at least one slice, which is to be imaged and which is inclined toward the system axis. The input unit cooperates with a control unit of the CT device such that the control unit adjusts the measuring unit in the direction of the system axis for scanning a volume of the examination subject so that the slice, which is to be imaged and which is inclined toward the system axis, is completely contained in the scanned volume. An electronic computer initially constructs planar tomograms from the data acquired during the scanning of the volume and constructs the tomogram of a slice, which is to be imaged and which is inclined toward the system axis, by multi-planar reconstruction from the planar tomograms.

In the inventive CT device, a mechanical tilting of the measuring unit is therefore not necessary for imaging slices that are inclined toward the system axis. Rather, the display of such inclined slices is digitally enabled by means of software by scanning the volume of the examination subject, which contains the slice to be imaged and which slice is inclined toward the system axis, and obtaining the tomogram of the desired slice that is inclined toward the system axis, by the known method of multi-planar reconstruction, from the tomograms of slices of the scanned volume that reside in planes at a right angle to the system axis and that have been reconstructed on the basis of the acquired data. Thus, the size of the scanned volume does not significantly exceed the size required for the acquisition of the slice that is to be imaged and that is inclined toward the system axis.

Not only is the mechanical outlay considerably reduced by avoiding the mechanical tilting of the measuring unit, since all mechanical components, which enable the tilting of the measuring unit, are avoided, but also a considerable facilitation of the control unit is also possible, since, for example safety checks regarding the danger of squeezing to the examination subject when tilting the gantry, can be reduced. The financial advantages that are achieved by the inventive structure are not only of importance for medical applications but also for industrial applications.

Further, the inventive CT device occupies less space, so that mobile use, for example on a motorized cart, is facilitated. Since the selection of the slice that is to be imaged and that is inclined toward the system axis ensues by means of software, a gain in time is also achieved when examinations are conducted, since the time required for the tilting of the measuring unit, which only ensues with low angular velocity, is saved.

Another advantage is that the diameter of the measuring opening of the measuring unit, through which the examination subject extends when an examination is conducted, does not represent a limitation for the maximum inclination that slices to be imagined can exhibit. Rather, it must only be observed that the diameter of the measuring opening is no larger than this necessary in order to be able to place an examination subject of a fixed maximal size in the measuring opening. This advantage is particularly beneficial with respect to corpulent patients. Besides, the examination subject or the support bed carrying the examination subject can be lowered in the measuring opening without any danger, so that there is no danger of collision as in the case of a mechanically tilted measuring unit. This is particularly beneficial with respect to the therapy planning.

When the tilting of the measuring unit is foregone, a support bed that is provided for the examination subject can be rigidly combined with the measuring unit, so that the outlay, which is required for the stabilization of the position of the center plane of the measuring system relative to the bed, is drastically reduced. Corresponding software modules can be omitted in the control unit, for example. Further, the outlay of testing that is required with respect to the initial operation and maintenance of the CT device is also reduced when a mechanical tilting of the measuring unit is foregone.

The inventive CT device thus enables significant cost savings.

In a version of the invention the CT device displays the tomogram of the slice to be imaged and which is inclined toward the system axis on a monitor, without prior display of the planar tomograms, and this display forms the basis for the acquisition of this inclined tomogram,.

In a preferred version of the invention, the input unit are allows entry of a spatial area that contains a number of slices that are inclined toward the system axis, so that it is possible to examine volumes that are inclined toward the system axis.

Also in a preferred embodiment, the input unit includes a display unit for displaying an X-ray shadow image (referred to as a topogram or "scout view"), which is picked up with the CT device and which is stored in the CT device, and a marking arrangement by means of which a spatial area, which contains at least one slice that is to be imaged and that is inclined toward the system axis or which contains a number of slices that are to be imaged and that are inclined toward the system axis, can be marked in the X-ray shadow image. It is thus assured that, in fact, the volume that is required imaging the slice(s) inclined toward the system axis is scanned, so that it is highly unlikely that examinations must be repeated or that the desired slice will be incompletely imaged.

In order to assure that, in fact, only the volume that is required for imaging a spatial area, which contains a slice or slices inclined toward the system axis, is scanned in so as to avoid unnecessary radiation loads, in an embodiment of the invention the computer determines an initial position and an end position on the basis of the entered position of the aforementioned spatial area. Between the initial position and the end position, the control unit adjusts the measuring unit in the direction of the system axis for scanning this spatial area.

If the slice, which is to be imaged and which is inclined toward the system axis, fills only one section of the image format of the display format on the monitor, in an embodiment of the invention the computer causes the tomogram to be displayed on the monitor in a format-filling manner, so that the full format of the monitor can be utilized, even when only details are to be imaged.

DESCRIPTION OF THE PREFERRED EMBODIMENTS

Figure 1:
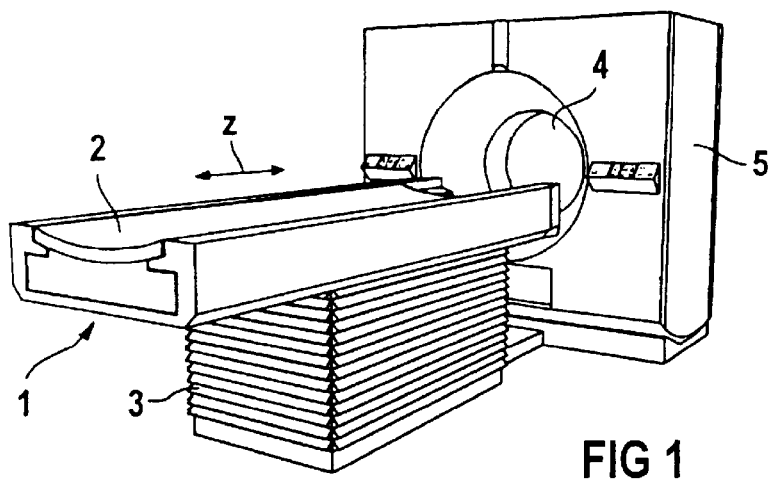
FIG. 1 shows an inventive CT device in a perspective illustration.

FIG. 1 shows an inventive CT device, having a patient bed 1 with a support plate 2 that is displaceable in the direction of its longitudinal axis, which is parallel to the system axis of the CT device in the direction of the double arrow z.

An examination subject, for example a patient 11 (see FIG. 2), lying on the support plate 2 can be positioned in the measuring opening 4 of a measuring unit 5 by longitudinal displacement of the support plate 2.

Figure 2:
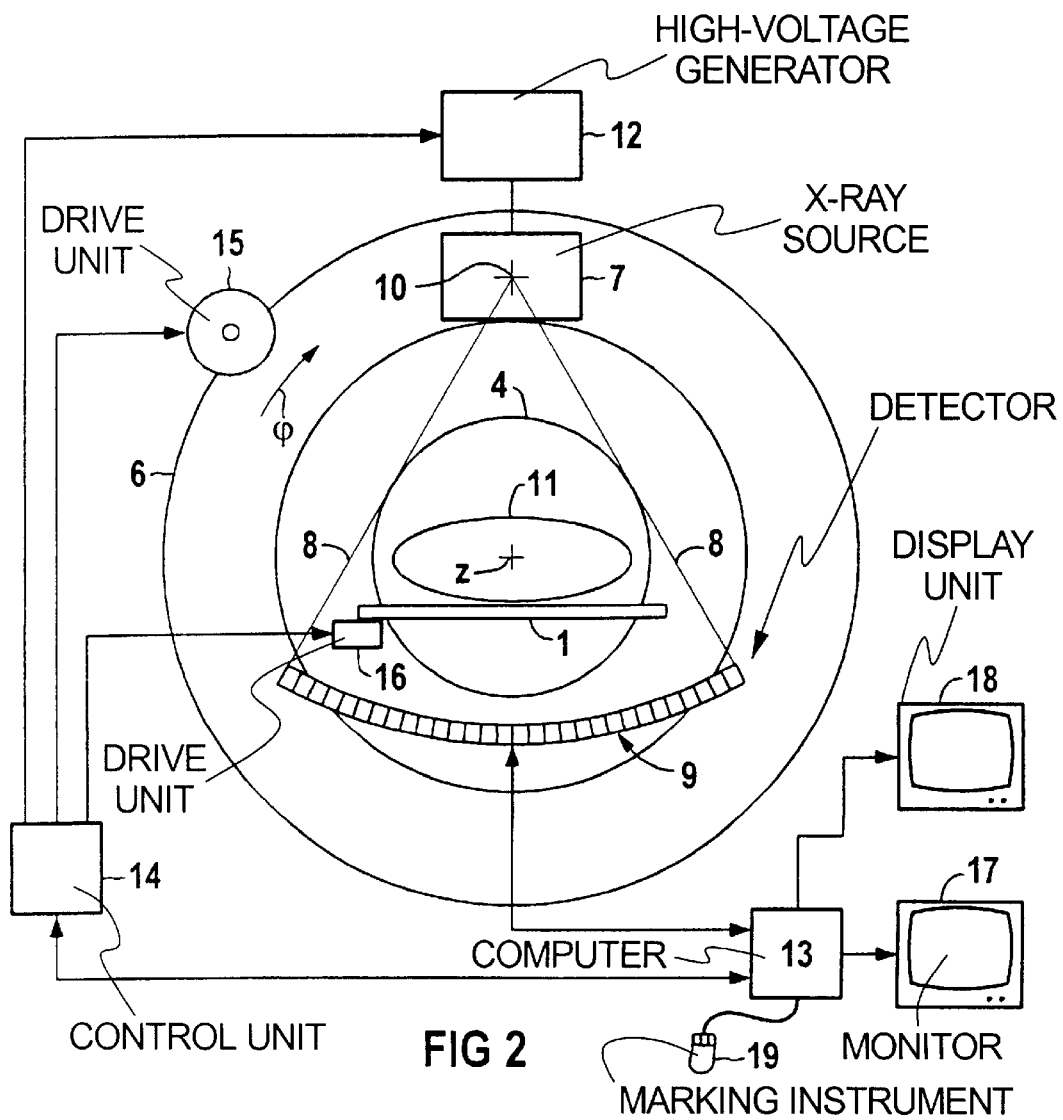
FIG. 2 schematically and with a block diagram, shows details of the CT of FIG. 1.

As can be seen from FIG. 2, the measuring unit 5 contains a rotary ring 6 that surrounds the measuring opening, on which an X-ray source 7 and a detector system 9, are mounted opposite to one another. In the exemplary embodiment, the detector system 9 is formed by a circularly curved row of 512 detector elements, for example.

The X-ray source 7 has a focus from which a fan-shaped X-ray bundle 8 emanates that is incident on the detector system 0. The X-ray source 7 is supplied by a high voltage generator 12.

For scanning a patient 11 lying on the support plate 2, the rotary ring 6 is rotated in the Φ-direction around the system axis, which axially extends through the measuring opening 4 and resides at a right angle to the plane of FIG. 2, and that such that the focus 10 of the X-ray source 7 moves on an orbit in a plane that resides at a right angle to the system axis. Thereby, the fan-shaped X-ray bundle 8 irradiates a planar slice of the patient 11, which planar slice is at a right angle to the system axis 2.

At predetermined angle positions, referred to as projection angles, the detector system 9 supplies data sets for the corresponding projections to an electronic computer 13 the computer 13 calculates the attenuation coefficients that belong to the picture elements of the slice of the patient 11 from the data sets, resulting from irradiation by the X-ray bundle 8.

Since the support plate 2 can be displaced in the direction of the system axis z, a volume of the patient 11 can be scanned by successively scanning a number of parallel slices that are preferably adjacent to one another (sequence scan) and transversal tomograms respectively corresponding to the scanned planar slices are constructed by the electronic computer 13 on the basis of known reconstruction algorithms.

Additionally, it is possible to scan a volume of the patient by continuously displacing the support plate 2 in the direction of the system axis z while the rotary ring 6 also continuously rotates. This preferably ensues with a constant ratio of rotational speed and translational speed, so that the focus 10 of the X-ray source 7 moves along a helical line around the patient 11 (spiral scan). On the basis of known spiral reconstruction algorithms, the electronic computer 13 calculates transversal tomograms of desired planar slices of the patient 11 from the thus-acquired data, which slices reside at a right angle to the system axis 2.

It is also possible to stop the rotation of the rotary ring 6 and to irradiate the patient 11 while displacing the support plate 2 in the direction of the system axis z. The electronic computer 13 calculates an X-ray shadow image from the data that are thereby provided by the detector system 9. The "viewing direction" of this X-ray shadow image is determined by the selected angle position.

For controlling the rotation of the rotary ring 6, the longitudinal movement of the support plate 2 and the X-ray source 7, a control unit 14 is provided, which actuates drives 15 and 16 which engage the rotary ring 6 and the support plate 2 and which actuates the high voltage generator 12.

A monitor 17 for the display of tomograms and a display unit 18 for the display of X-ray shadow images are connected to the electronic computer 13. Further, an input unit (a mouse 19 in the exemplary embodiment) is connected to the computer 13 in order to be able to undertake markings in the X-ray shadow image displayed on the display unit 18.

It is conventional to fashion the measuring unit 5 around a horizontally extending axis such that it can be tilted in order to be able to prepare tomograms of slices that do not extend at an right angle to the system axis z but are inclined relative to the system axis. Such a tilting capability is not provided in the case of the inventive CT device. Rather, for preparing tomograms of slices inclined toward the system axis z, is operated the inventive CT device as follows:

As described above, an X-ray shadow image of the diagnostically relevant area of the patient 11 is initially prepared. This said X-ray shadow image is displayed on the display unit 18. For example, by "clicking" on two points in the X-ray shadow image by means of the mouse 19, the course of a slice that is desired to be imaged and that is generally inclined toward the system axis z is prescribed. The computer 13 subsequently fades-in the corresponding line (in dashed lines in FIG. 3, designated as SE) into the X-ray shadow image. The slice plane of the selected slice resides at a right angle to the image plane of the X-ray shadow image.

Figure 3:
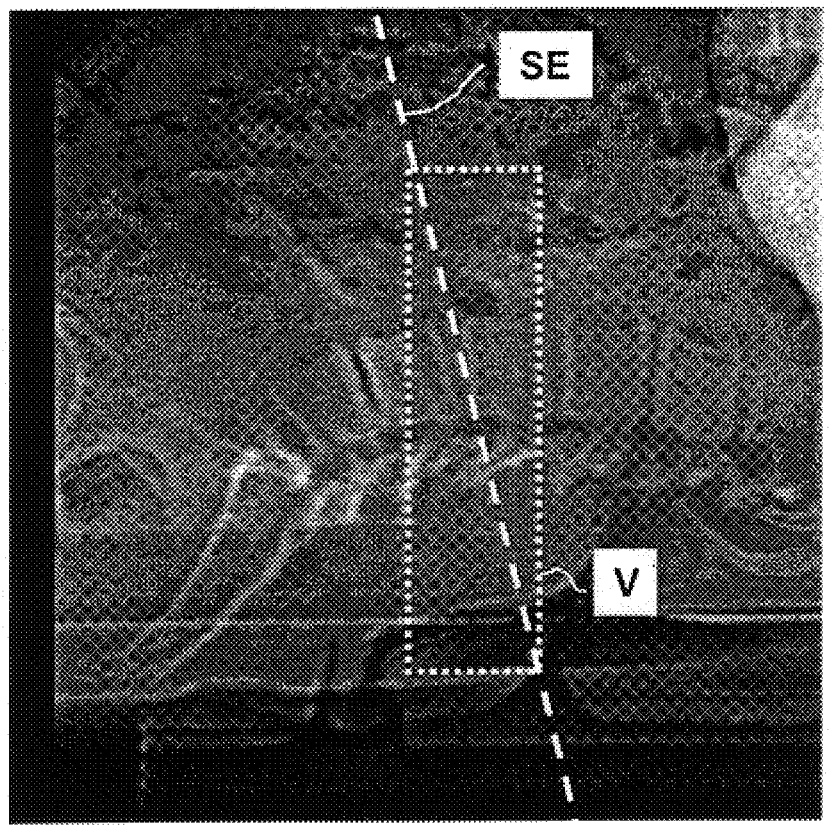
FIG. 3 is an X-ray shadow image that serves the purpose of marking a slice that is to be imaged and that is inclined toward the system axis in accordance with the invention.

As shown in FIG. 3, it is further possible to mark a rectangle (illustrated with dotted lines and designated V) by means of the mouse 19 when the desired tomogram does not have to occupy the entire area of the slice plane contained in the X-ray shadow image.

Now, the volume that corresponds to the entire area of the slice plane SE contained in the X-ray shadow image, or the volume of the patient 11 that corresponds to the marking V, must be scanned in the course of a sequence scan or spiral scan in order to be able to acquire the desired tomogram. The volume contains the slice to be imaged, or the area of the slice to be imaged. For that purpose, the electronic computer 13, from the inputs according to FIG. 3, calculates the initial point and the end point of the movement with which the support plate 2, relative to the measuring unit 5, must be displaced in the direction of the system axis z and initially places the support plate 2 in the initial position. Proceeding from the initial position, the support plate 2 is displaced in the direction of the system axis z in its end position given scanning of the patient 11 by the X-ray bundle 8.

Figure 4:
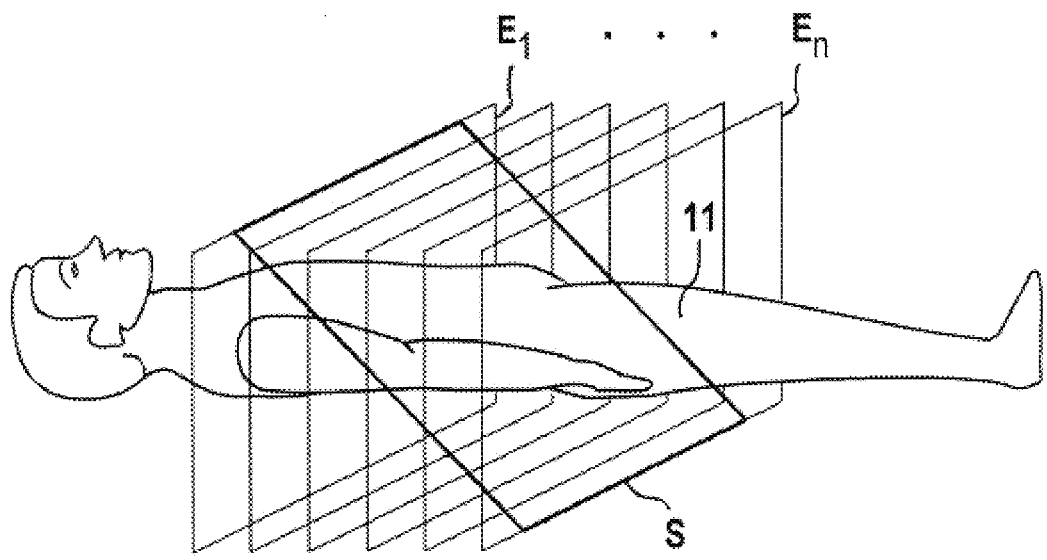
FIG. 4 is a diagram that shows the acquisition of the tomogram according to FIG. 3.

The electronic computer 13 reconstructs a number of tomograms of adjacent, planar slices residing at a right angle to the system axis z from the acquired data (designated as $E_1$ through $E_n$ in FIG. 4). The electronic computer 13 determines the data from these tomograms, this data belonging to the desired slice S that is to be imaged that extends in an inclined manner toward the system axis z, and constructs a tomogram that is displayed on the monitor 17. For a desired image resolution, any lacking data can be acquired by interpolation from the data of tomograms that belong to neighboring slices $E_1$ through $E_n$.

The tomograms of the slices $E_1$ through $E_n$ are generally not displayed. Rather, the tomogram of the slice S, which is to be imaged and which is inclined toward the system axis z, is immediately displayed on the monitor 17 without delay.

The above described procedure is known as "multi-planar reconstruction" (MPR) and is described in German OS 195 41 500, for example.

Figure 5:
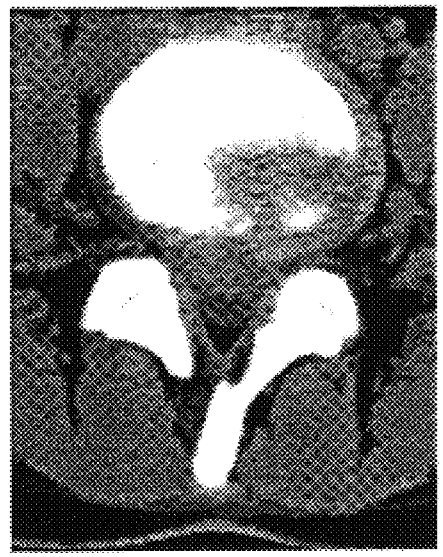
FIG. 5 is a tomogram of a slice inclined toward the system axis which is generated by means of the inventive CT device.

FIG. 5 shows an example of a tomogram of a slice that is inclined toward the system axis z, which is acquired in the described way.

Whereas the entire lumbar spinal column is shown in the X-ray shadow image according to FIG. 3, FIG. 5 shows the slice through a lumbar vertebra in a format-filling enlargement, this slice being inclined toward the system axis z and which is corresponding to the slice plane SE. The format-filling enlargement is realized by the electronic computer 13 by means of a know zoom function.

Figure 6:
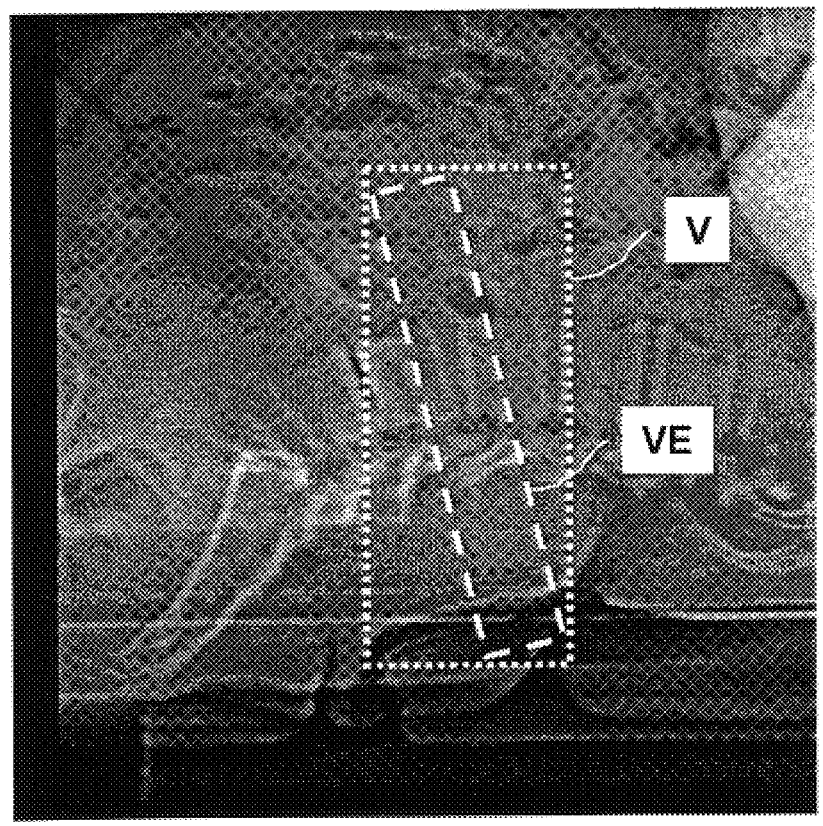
FIG. 6 is an X-ray shadow image that serves the purpose of marking a volume that contains a number of slices, which are to be imaged and which are inclined toward the system axis in accordance with the invention.

Alternatively to the above described procedure, it is possible, as shown in FIG. 6, to mark an area that contains a number of slices that are to be imaged and that are inclined toward the system axis. This ensues as shown in FIG. 6, by marking a rectangular area in the X-ray shadow image using the mouse 19, and this rectangular area is faded into the X-ray shadow image shown on the display unit 18 in the form of a broken line (designated VE in FIG. 6) by means of the electronic computer 13. The volume that contains the slice planes then exhibits boundary surfaces residing at a right angle to the image plane of the X-ray shadow image.

Similar to the previously described procedure, a scanning of the volume V, which contains the relevant area of the patient 11 and which, according to FIG. 6, is faded into the X-ray shadow image as a dotted rectangle by the computer 13, now ensues in the form of a sequence scan or spiral scan.

Analogously to the previously described procedure, the electronic computer 13 then reconstructs tomograms of parallel slices, which are inclined toward the system axis z, on the basis of the required data.

In the exemplary embodiment, an electronic control unit 14 that controls the CT device, and the electronic computer 13 that generates an image, are provided. Alternatively, it is possible to provide one single control unit and computing unit, which assumes not only the task of the control but also of image generation.

A separate monitor 17 and a display unit 18 need not necessarily be provided for purposes of showing the tomograms and the X-ray shadow images, as in the case of the exemplary embodiment. Instead, a common display can be provided, such a common display not only presenting tomograms but also X-ray shadow images and which, depending on the operational mode of the CT device, either shows a tomogram or an X-ray shadow image.

The invention is described above in the context of a CT device of the third generation as an example, wherein the X-ray source and the detector system rotate together. It is also possible to inventively fashion CT devices of the fourth generation, wherein a rotating X-ray source cooperates with a stationary ring of detector elements.

The above described CT device has a detector system with a single row of detector elements. In the context of the invention, a number of rows of detector elements can be provided instead, for example 16 rows per 800 detector elements, or matrix-like arrangements of detector systems having detector elements can be provided. In this case, a pyramidal X-ray bundle, or a conical X-ray bundle, that is adapted to the arrangement of the detector elements proceeds from the X-ray source 7, rather than a fan-shaped X-ray bundle 8.

The exemplary embodiment is directed to a medical application of an inventive CT device, however, the invention also is applicable to non-medical fields, such as luggage examination and nondestructive material checks, for example.

It is possible in the framework of the invention to use a patient support table having a support plate, for examinations that require this, which can be placed into a position that is inclined toward the system axis.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography device for imaging slices that are inclined toward a system axis, comprising:

a measuring unit having a radiation source with a focus, at least said focus being displaceable around a system axis, and a detector system on which radiation from said radiation source is incident for irradiating an examination subject disposed between said radiation source and said detector system from a plurality of different projection angles;

a support adapted to receive an examination subject, said support and said measuring unit being adjustable relative to each other in a direction of said system axis, while displacing said focus, for scanning a volume of an examination subject;

an input unit for entering a position of at least one slice which is to be imaged and which is inclined toward said system axis;

a control unit connected to said input unit for relatively adjusting said measuring unit and said support in said direction of said system axis for scanning a scanned volume so that said at least one slice is completely contained in said scanned volume, said detector system detecting a plurality of projection data sets, respectively at said projection angles, during scanning of said scanned volume; and an electronic computer supplied with said projection data sets for initially calculating planar tomograms from said projection data sets and for, from said planar tomograms, reconstructing said slice that is inclined toward the system axis by multi-planar reconstruction.

2. A computed tomography device as claimed in claim 1 further comprising a display connected at least to said input unit which displays a tomogram of said at least one slice which is inclined toward said system axis, without displaying said planar tomograms.

3. A computed tomography device as claimed in claim 1 wherein said input unit comprises means for entering a spatial area comprising a plurality of slices to be imaged and which are each inclined toward said system axis.

4. A computed tomography device as claimed in claim 1 wherein said radiation source and said detector system are operable by said control unit to produce an X-ray shadow image of an examination subject, and wherein said control unit stores said X-ray shadow image, and wherein said input unit includes a display and is connected to said control unit for retrieving said X-ray shadow image and displaying said X-ray shadow image on said display, and wherein said input unit includes a marking instrument for marking a spatial area in said X-ray shadow image on said display which includes said at least one slice which is to be imaged and which is inclined toward said system axis.

5. A computed tomography device as claimed in claim 4 wherein said marking instrument allows marking of a spatial area in said X-ray shadow image on said display which contains a plurality of slices to be imaged and each of which is inclined toward said system axis.

6. A computed tomography device as claimed in claim 5 wherein said input unit is connected to said computer and wherein said computer determines an initial position and an end position, dependent on said spatial area, for said relative movement between said measurement unit and said support for scanning said scanned volume, and supplies a signal to said control unit for controlling said relative movement to begin at said initial position and to end at said end position.

7. A computed tomography device as claimed in claim 1 further comprising a display connected to said computer, said displaying having an image format in which images are displayed on said display and wherein, if said slice occupies only a portion of said image format, said computer causes said slice to be displayed on said display so as to completely occupy said image format.

* * * * *